(12) United States Patent
Svetic

(10) Patent No.: US 7,942,853 B2
(45) Date of Patent: May 17, 2011

(54) FLUID CHAMBER

(75) Inventor: Ralph E. Svetic, Costa Mesa, CA (US)

(73) Assignee: Alcon, Inc., Hunenberg (CH)

( * ) Notice: Subject to any disclaimer, the term of this patent is extended or adjusted under 35 U.S.C. 154(b) by 573 days.

(21) Appl. No.: 11/329,800

(22) Filed: Jan. 11, 2006

(65) Prior Publication Data

US 2007/0161954 A1 Jul. 12, 2007

(51) Int. Cl.
*A61M 1/00* (2006.01)
(52) U.S. Cl. ............ 604/122; 604/131; 95/262; 96/204; 96/215; 96/220
(58) Field of Classification Search ............... 604/118, 604/122, 123, 131; 417/477.2, 313; 95/260, 95/262; 96/204, 207, 215, 220
See application file for complete search history.

(56) References Cited

U.S. PATENT DOCUMENTS

| | | |
|---|---|---|
| 4,140,118 A | 2/1979 | Jassawalla |
| 4,187,057 A | 2/1980 | Xanthopoulos |
| 4,479,761 A | 10/1984 | Bilstad et al. |
| 4,493,706 A | 1/1985 | Borsanyi et al. |
| 4,530,647 A | 7/1985 | Uno |
| 4,537,561 A | 8/1985 | Xanthopoulos |
| 4,680,445 A * | 7/1987 | Ogawa ............................ 392/470 |
| 4,713,051 A | 12/1987 | Steppe et al. |
| 4,758,238 A | 7/1988 | Sundblom et al. |
| 4,768,547 A | 9/1988 | Danby et al. |
| 4,795,440 A | 1/1989 | Young et al. |
| 4,798,090 A | 1/1989 | Heath et al. |
| 4,798,580 A | 1/1989 | DeMeo et al. |
| 4,838,865 A | 6/1989 | Flank et al. |
| 4,861,242 A | 8/1989 | Finsterwald |
| 4,921,477 A | 5/1990 | Davis |
| 4,923,375 A | 5/1990 | Ejlersen |
| 4,935,005 A | 6/1990 | Haines |
| 4,963,131 A | 10/1990 | Wortrich |
| 5,041,096 A | 8/1991 | Beuchat et al. |
| 5,056,992 A | 10/1991 | Simons et al. |
| 5,106,366 A | 4/1992 | Steppe |
| 5,195,960 A | 3/1993 | Hossain et al. |
| 5,207,647 A | 5/1993 | Phelps |
| 5,267,956 A | 12/1993 | Beuchat |
| 5,302,093 A | 4/1994 | Owens et al. |
| 5,364,342 A | 11/1994 | Beuchat et al. |
| 5,392,653 A | 2/1995 | Zanger et al. |

(Continued)

FOREIGN PATENT DOCUMENTS

EP 0208955 1/1987

(Continued)

OTHER PUBLICATIONS

European Search Report for EP 06122959.7, Publication No. EP1779878, 2 pages.

(Continued)

*Primary Examiner* — Theodore J Stigell
*Assistant Examiner* — Emily Schmidt
(74) *Attorney, Agent, or Firm* — Darien Reddick

(57) ABSTRACT

A fluid chamber having an inlet and an outlet at the top of the chamber. The inlet is arrange so that fluid entering the chamber at the inlet sweeps the top of the chamber so as to direct any air bubbles naturally collecting at the top of the chamber or which may be trapped in the entering fluid stream toward the outlet.

22 Claims, 4 Drawing Sheets

U.S. PATENT DOCUMENTS

| | | |
|---|---|---|
| 5,403,277 A | 4/1995 | Dodge et al. |
| 5,429,485 A | 7/1995 | Dodge |
| 5,429,602 A | 7/1995 | Hauser |
| 5,460,490 A | 10/1995 | Carr et al. |
| 5,470,312 A | 11/1995 | Zanger et al. |
| 5,499,969 A | 3/1996 | Beuchat et al. |
| 5,518,378 A | 5/1996 | Neftel et al. |
| 5,586,438 A | 12/1996 | Fahy |
| 5,588,815 A | 12/1996 | Zaleski, II |
| 5,634,907 A | 6/1997 | Rani et al. |
| 5,709,539 A | 1/1998 | Hammer et al. |
| 5,746,708 A | 5/1998 | Giesler et al. |
| 5,746,719 A | 5/1998 | Farra et al. |
| 5,759,017 A | 6/1998 | Patton et al. |
| 5,810,204 A | 9/1998 | Devlin et al. |
| 5,897,524 A | 4/1999 | Wortrich et al. |
| 5,906,598 A | 5/1999 | Gielser et al. |
| 5,910,110 A | 6/1999 | Bastable |
| 5,927,956 A | 7/1999 | Lim et al. |
| 5,996,634 A | 12/1999 | Dennehey et al. |
| 6,012,999 A | 1/2000 | Patterson |
| 6,059,544 A | 5/2000 | Jung et al. |
| 6,059,765 A | 5/2000 | Cole et al. |
| 6,129,699 A | 10/2000 | Haight et al. |
| 6,261,283 B1 | 7/2001 | Morgan et al. |
| 6,272,930 B1 | 8/2001 | Crozafon et al. |
| 6,293,926 B1 | 9/2001 | Sorensen et al. |
| 6,494,694 B2 * | 12/2002 | Lawless et al. ............... 417/479 |
| 6,572,349 B2 | 6/2003 | Sorensen et al. |
| 6,592,737 B1 | 7/2003 | Robertson |
| 6,827,709 B2 | 12/2004 | Fujii |
| 6,962,488 B2 | 11/2005 | Davis et al. |
| 2003/0190244 A1 | 10/2003 | Davis et al. |
| 2005/0186098 A1 | 8/2005 | Davis et al. |
| 2007/0098578 A1 | 5/2007 | Morgan |
| 2008/0271741 A1 | 11/2008 | Graham et al. |

FOREIGN PATENT DOCUMENTS

| | | |
|---|---|---|
| EP | 1213033 | 6/2002 |
| EP | 1779878 | 5/2007 |
| JP | 07-505542 | 1/1993 |
| JP | 09-178535 | 10/1996 |
| JP | 2000-510239 | 8/2000 |
| JP | 2001-165054 | 6/2001 |
| WO | WO 93/24082 | 12/1993 |
| WO | WO 93/24817 | 12/1993 |

OTHER PUBLICATIONS

European Search Report for EP 06122960.5, Publication No. EP1779879, 2 pages.

* cited by examiner

FLUID CHAMBER

BACKGROUND OF THE INVENTION

The present invention relates generally to fluid pressure sensing chambers and more specifically to fluid pressure sensing chambers used in ophthalmic surgical equipment.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced by an artificial lens.

A typical ultrasonic surgical device suitable for ophthalmic procedures consists of an ultrasonically driven handpiece, an attached cutting tip, and irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draws aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece by flexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve.

In use, the ends of the cutting tip and irrigating sleeve are inserted into a small incision of predetermined width in the cornea, sclera, or other location. The cutting tip is ultrasonically vibrated along its longitudinal axis within the irrigating sleeve by the crystal-driven ultrasonic horn, thereby emulsifying the selected tissue in situ. The hollow bore of the cutting tip communicates with the bore in the horn that in turn communicates with the aspiration line from the handpiece to the console. A reduced pressure or vacuum source, usually a peristaltic pump, in the console draws or aspirates the emulsified tissue from the eye through the open end of the cutting tip, the cutting tip and horn bores and the aspiration line and into a collection device. The aspiration of emulsified tissue is aided by a saline flushing solution or irrigant that is injected into the surgical site through the small annular gap between the inside surface of the irrigating sleeve and the cutting tip.

Prior art devices have used sensors that detect irrigation pressure or aspiration vacuum. Based on the information from these sensors, the surgical console can be programmed to respond in order to make the surgical procedure more efficient and safer. In order to reduce the risk of contamination by the aspirated fluid, recent surgical systems use closed pressure sensors, in which the fluid does not come into contact with the load cell or other device used to sense the fluid pressure. One such pressure sensor is illustrated in U.S. Pat. No. 5,392,653 (Zanger, et al.). Overall performance of such closed pressure sensors, however; depends in large part on purging all of the air from the system. Air is much more compressible than the irrigating solution used in surgery, and air pockets or bubbles add compliance to the system. Compliance results in undesirable pressure variations and fluctuations. Common methods of assisting in purging air from sealed liquid systems (or "priming" the system) include avoiding sharp edges and abrupt shape changes within the system as well as filling the system with liquid from the bottom or low point of the system. This allows the air to escape out of the top of the system as the systems fills with liquid from below because, as one skilled in the art will recognize, saline solutions are heavier than air. The inventors of the present invention have discovered that the initial priming of a pressure sensor chambers found within closed surgical fluidic systems is relatively easy, but if bubbles of air are allowed to enter the chamber (for example, if the surgical handpiece is changed mid-procedure), these air bubbles are extremely difficult to purge from the system. This difficulty is the result of the surface tension of the air bubble (as opposed to the unencapsulated air generally involved in the initial priming of the system) causing the bubble to be relatively robust and not easily broken and drawn out of the pressure sensing chamber once introduced. In addition, the surface tension of the liquid "film" surrounding the air bubble causes the bubble to have a "tackiness", causing the bubble to want to stick or adhere to surfaces within the system and resist further movement, even with very high flow rates. One reference, U.S. Pat. No. 6,059,765 (Cole, et al.) has suggested that certain chamber shapes and outlet locations may assist in the removal of air from surgical systems. The inventors have found that the chamber shapes and designs discussed in this reference are insufficient to assure that air bubbles can be purged from the system because fluid flow through the chamber tends to follow defined pathways. Fluid contained within the chamber out side of these defined pathways tends to be relatively stagnant. Any air bubbles contained within these stagnant pools of fluid will adhere to the boundaries of the chamber and resist being purged from the chamber.

Accordingly, a need continues to exist for a pressure sensing chamber that helps purge air bubbles that may be introduced into the chamber.

BRIEF SUMMARY OF THE INVENTION

The present invention improves upon prior art fluid chamber designs by providing a fluid chamber having an inlet and an outlet at the top of the chamber. The inlet is arrange so that fluid entering the chamber at the inlet sweeps the top of the chamber so as to direct any air bubbles naturally collecting at the top of the chamber or which may be trapped in the entering fluid stream toward the outlet.

One objective of the present invention is to provide a fluid chamber that is easy to prime.

Another objective of the present invention is to provide a fluid chamber that does not permit air bubbles to become trapped in the chamber.

Yet another objective of the present invention is to provide a fluid chamber having an inlet arranged so that fluid entering the chamber at the inlet sweeps the top of the chamber.

DETAILED DESCRIPTION OF THE INVENTION

Figure 1:
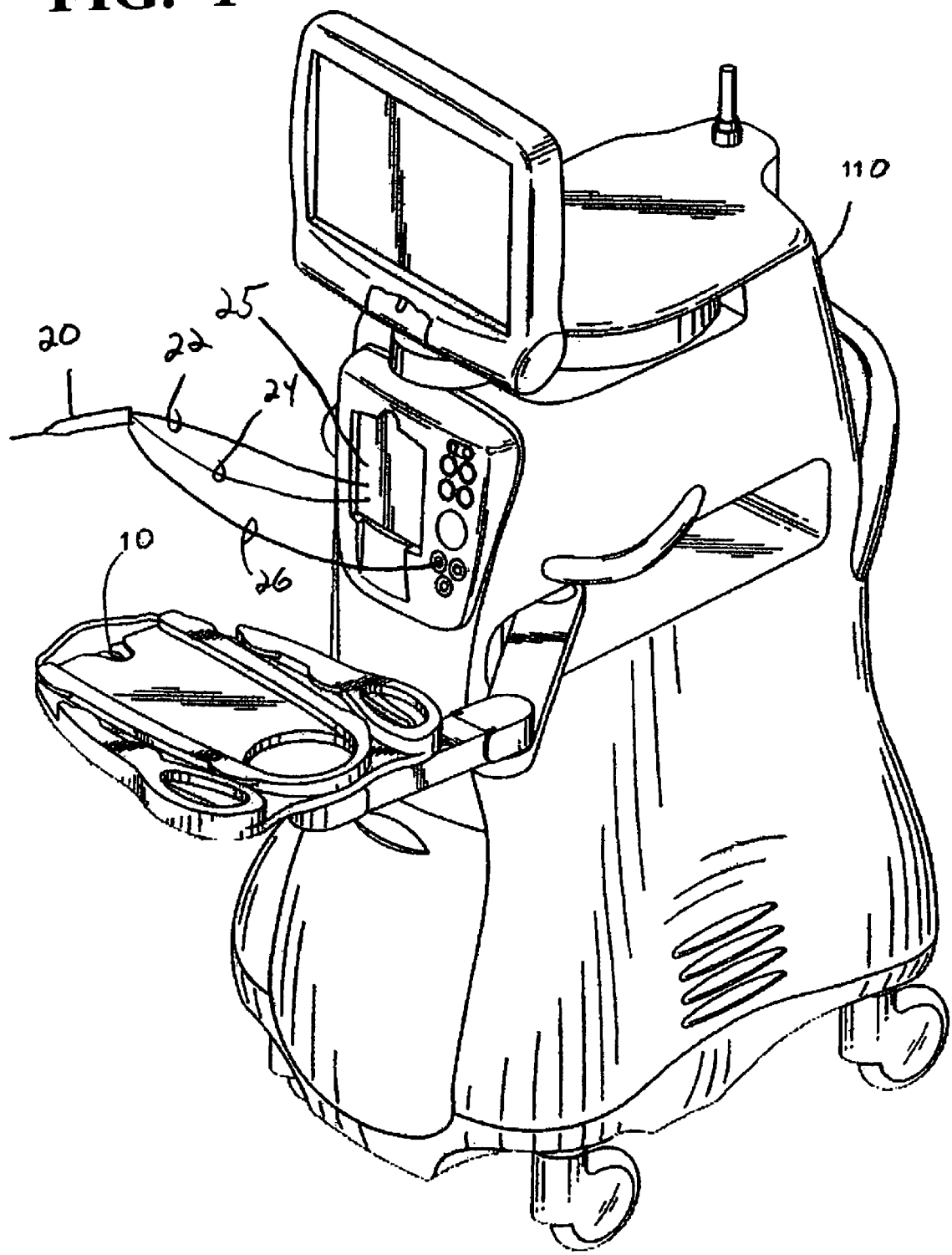
FIG. 1 is a perspective view of a surgical system that may be used with the fluid chamber of present invention.
Figure 2:
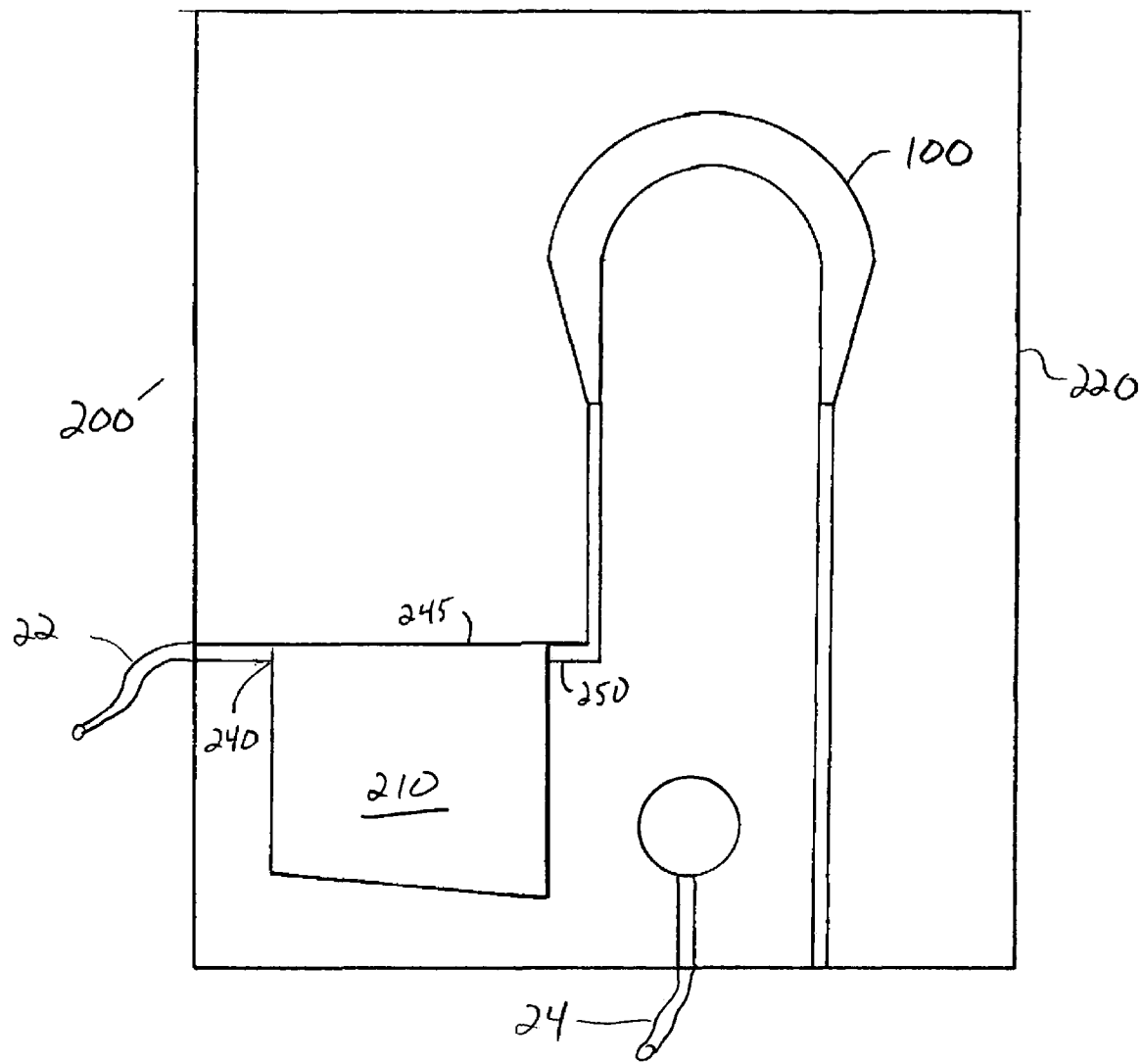
FIG. 2 is a schematic representation of a surgical cassette that may be used with the fluid chamber of the present invention.

As best seen in FIG. 1, commercially available surgical systems generally include surgical console 110 having attached, adjustable tray 10 and handpiece 20 attached to console 110 by aspiration tubing 22, irrigation tubing 24 and power cable 26. Power to handpiece 20 as well as the flows of irrigation and aspiration fluid is controlled by console 110, which contains appropriate hardware and software, such as power supplies, pumps, pressure sensors, valves, all of which are well-known in the art. As best seen in FIG. 2, cassette 200 that may be used with the present invention receives aspiration tubing 22 and irrigation tubing 24 and is installed within cassette receiving portion 25 of console 110. Cassette 200 contains pumping segment 100 and fluid chamber 210 which may be a pressure sensing chamber and may consist of a hollow void formed within body 220 of cassette 200. Cassette 200 may be any of a variety of commercially available surgical cassettes such as the INFINITI® Fluid Management System available from Alcon Laboratories, Inc., Fort Worth, Tex. Body 220 is generally molded from a suitable thermoplastic.

Figure 3:
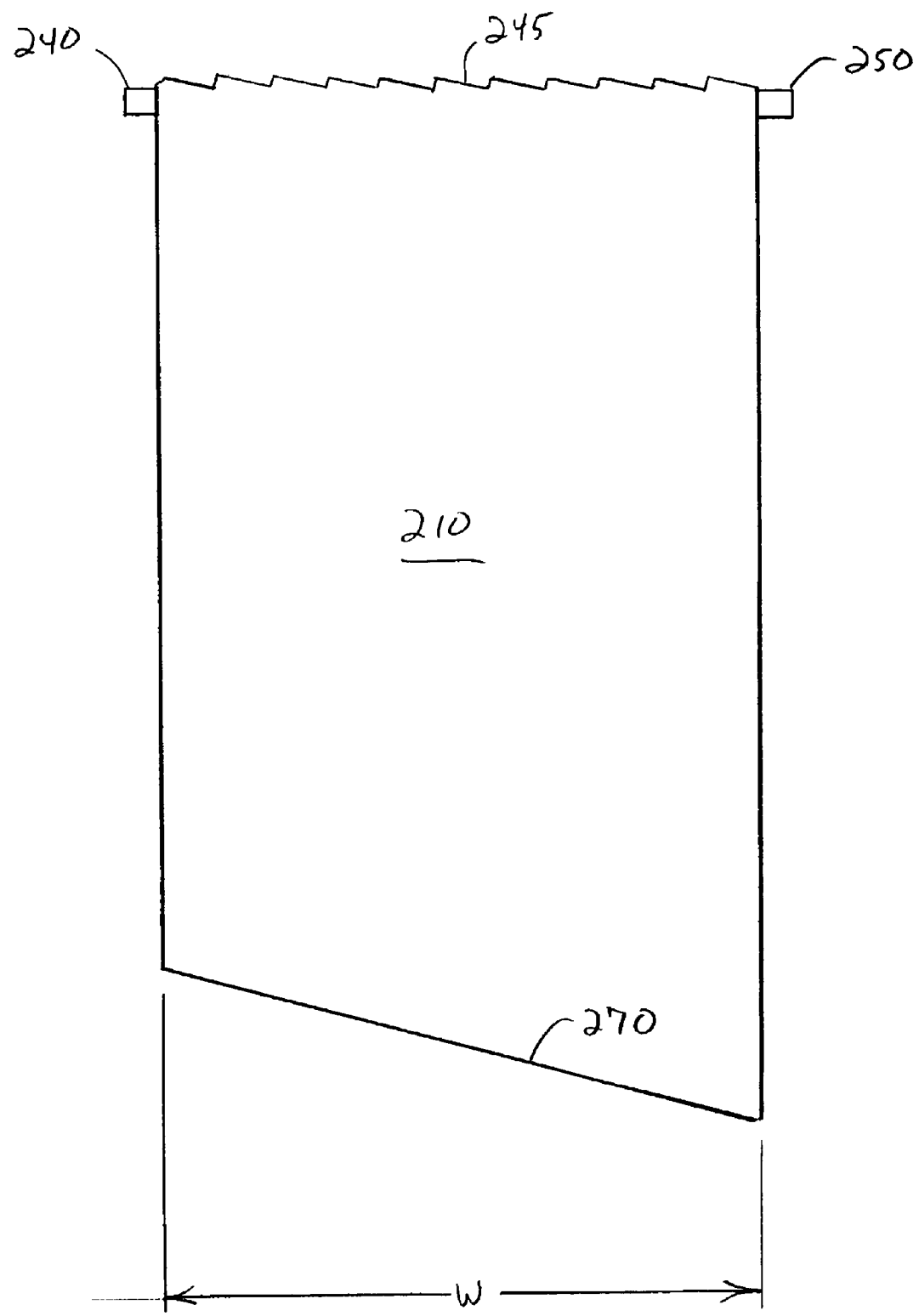
FIG. 3 is an enlarged cross-sectional view of the fluid chamber of the present invention.
Figure 4:
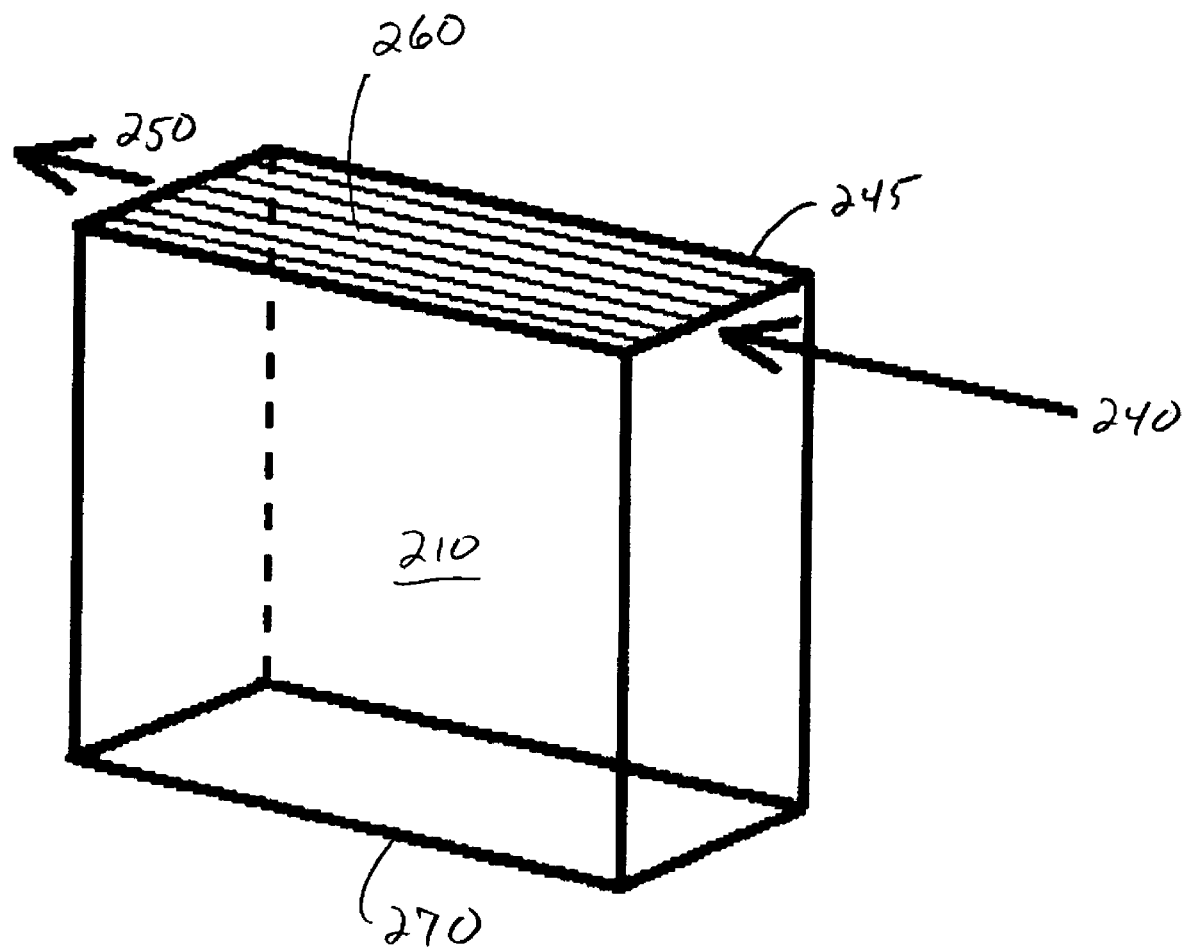
FIG. 4 is an enlarged, schematic, perspective view of the fluid chamber of the present invention.

As best seen in FIG. 3, chamber 210 contains inlet 240 and outlet 250 that enter chamber 210 at top 245 of chamber 210. Outlet 250 is in fluid communication with pumping segment 100. Inlet 240 is preferably aligned with outlet 250 at top 245 so that fluid entering chamber 210 from inlet 240 sweeps across top 245 directly toward outlet 250. Inlet 240 may be shaped so that fluid entering into chamber 210 fans out to cover the entire depth of top 245. Chamber 210 is generally rectangular in shape, preferably greater in width W greater than in depth (the direction perpendicular to or into the plane of the paper). Top 245 preferably is molded with a roughened or "pointy" surface, such as by molding in a series of half-round scallops or a series of shallow undercuts producing a saw tooth-like pattern. Such a construction reduces the contact surface area between top 245 and any bubbles that enter chamber 210. As best seen in FIG. 4, top 245 may be formed so as to contain a series of parallel channels 260 that run between inlet 240 and outlet 250. Channels 260 help direct fluid flow from inlet 240 to outlet 250. As seen in FIG. 3, bottom 270 of chamber 210 may be formed with a slope to improve manufacturability of chamber 210.

This description is given for purposes of illustration and explanation. It will be apparent to those skilled in the relevant art that modifications may be made to the invention as herein described without departing from its scope or spirit.

I claim:

1. A fluid chamber, comprising:
   a) a top comprising a plurality of sloping surfaces forming a plurality of pointed edges where adjacent sloping surfaces intersect, the plurality of sloping surfaces forming a saw tooth-like pattern;
   b) an inlet at a top of the chamber; and
   c) an outlet located opposite the inlet at the top of the fluid chamber so that fluid flowing into the chamber through the inlet flows directly across the top and toward the outlet, the top being formed from the plurality of sloping surfaces along a length of the fluid chamber from the inlet to the outlet,
   wherein adjacent sloping surfaces define a ridge, wherein the ridges are identical to each other, and wherein each ridge has a constant cross-sectional shape.

2. The chamber of claim 1 wherein the plurality of pointed edges minimize an air bubble contact area of the top.

3. A cassette, comprising:
   a) a body;
   b) a fluid chamber formed in the body, the fluid chamber being formed as a hollow void in the body;
   c) an inlet in the fluid chamber at a top of the fluid chamber, the top of the fluid chamber comprising a plurality of sloping surfaces forming a plurality of pointed edges where adjacent sloping surfaces intersect, the plurality of sloping surfaces forming a saw tooth-like pattern;
   d) an outlet in the fluid chamber, the outlet located opposite the inlet at the top of the fluid chamber so that fluid flowing into the chamber through the inlet flows directly across the top and toward the outlet, the top being formed from the plurality of sloping surfaces along a length of the fluid chamber from the inlet to the outlet,
   wherein adjacent sloping surfaces define a ridge, wherein the ridges are identical to each other, and wherein each ridge has a constant cross-sectional shape.

4. The cassette of claim 3 wherein the cassette further comprises a pumping segment in fluid communication with the outlet.

5. The cassette of claim 3 further comprising an aspiration tubing connected to the cassette.

6. The cassette of claim 4 further comprising an aspiration tubing connected to the cassette and in fluid communication with the pumping segment.

7. A surgical system, comprising:
   a) a surgical console having a cassette receiving portion;
   b) a surgical cassette received by the console in the cassette receiving portion, the cassette having
      i) a body;
      ii) a fluid chamber formed in the body;
      iii) an inlet in the fluid chamber at a top of the fluid chamber, the top comprising a plurality of sloping surfaces forming a plurality of pointed edges where adjacent sloping surfaces intersect, the plurality of sloping surfaces forming a saw tooth-like pattern; and
      iv) an outlet in the fluid chamber, the outlet located opposite the inlet at the top of the fluid chamber so that fluid flowing into the chamber through the inlet flows directly across the top and toward the outlet, the top being formed from the plurality of sloping surfaces along a length of the fluid chamber from the inlet to the outlet,
         wherein adjacent sloping surfaces define a ridge, wherein the ridges are identical to each other, and wherein each ridge has a constant cross-sectional shape.

8. The surgical system of claim 7 wherein the cassette further comprises a pumping segment.

9. The surgical system of claim 7 further comprising an aspiration tubing connected to the cassette and in fluid communication with the inlet.

10. The surgical system of claim 7 further comprising an aspiration tubing connected to the cassette and in fluid communication with the pumping segment.

11. The fluid chamber of claim 1, wherein fluid flowing into the chamber through the inlet directly across the top and toward the outlet defines a fluid flow path and wherein the plurality of pointed edges are disposed transversely to the fluid flow path.

12. The fluid chamber of claim 1, wherein the fluid flow path is free of obstructions.

13. The fluid chamber of claim 1, wherein the top is formed from a rigid material.

14. The fluid chamber of claim 1, wherein the top further comprises a plurality of parallel channels extending from the inlet to the outlet.

15. The cassette of claim 3, wherein fluid flowing into the chamber through the inlet directly across the top and toward the outlet defines a fluid flow path and wherein the plurality of sloping surfaces extend in a direction transverse to the fluid flow path.

16. The cassette of claim 3, wherein the fluid flow path is free of obstructions.

17. The cassette of claim 3, wherein the plurality of sloping surfaces are formed from a rigid material.

18. The cassette of claim 3, wherein the top further comprises a plurality of parallel channels extending from the inlet to the outlet.

19. The surgical system of claim 7, wherein fluid flowing into the chamber through the inlet directly across the top and toward the outlet defines a fluid flow path and wherein the plurality of sloping surfaces extend in a direction transverse to the fluid flow path.

20. The surgical system of claim 7, wherein the fluid flow path is free of obstructions.

21. The surgical system of claim 7, wherein the plurality of sloping surfaces are formed from a rigid material.

22. The surgical system of claim 7, wherein the top further comprises a plurality of parallel channels extending from the inlet to the outlet.

* * * * *